United States Patent [19]

Pollak et al.

[11] Patent Number: 4,746,016

[45] Date of Patent: May 24, 1988

[54] BLADE REMOVAL AND/OR MOUNTING MECHANISM AND DISPENSER, EXTRACTOR-DISPOSAL APPARATUS INCLUDING SAME

[75] Inventors: Stanley B. Pollak, Huntington, N.Y.; William Blasnik, Englewood, N.J.

[73] Assignee: The Research Foundation of State University of New York, Albany, N.Y.

[21] Appl. No.: 31,094

[22] Filed: Mar. 26, 1987

[51] Int. Cl.$^4$ .............................................. B65D 83/00
[52] U.S. Cl. .................................... 206/356; 29/239; 29/270; 30/339; 206/359; 206/370
[58] Field of Search ................................ 206/352-359, 206/363, 370, 366, 438; 30/40.2, 339; 29/235, 239, 267, 269, 270

[56] References Cited

U.S. PATENT DOCUMENTS

| | | |
|---|---|---|
| D. 264,882 | 6/1982 | Thompson . |
| 3,172,316 | 3/1965 | Grieshaber . |
| 4,106,620 | 8/1978 | Brimmer et al. . |
| 4,120,397 | 10/1978 | Neumann . |
| 4,168,777 | 9/1979 | Gaskell et al. ...................... 206/370 |
| 4,180,162 | 12/1979 | Magney . |
| 4,270,416 | 6/1981 | Thompson . |
| 4,318,473 | 3/1982 | Sandel . |
| 4,344,532 | 8/1982 | Eldridge, Jr. et al. . |
| 4,378,624 | 4/1983 | Klingenberg . |
| 4,386,457 | 6/1983 | Coombs . |
| 4,395,807 | 8/1983 | Eldridge, Jr. et al. ............... 29/239 |
| 4,466,539 | 8/1984 | Frauenhoffer . |
| 4,523,679 | 6/1985 | Paikoff et al. ...................... 206/438 |

Primary Examiner—Jimmy G. Foster
Attorney, Agent, or Firm—Hoffmann & Baron

[57] ABSTRACT

A mechanism for mounting and removing a blade having an elongated slot mounting means from a blade handle which has a mounting boss for insertion into the elongated slot. The mechanism includes a handle guide forming one side of a passageway for insertion of the handle therethrough, the handle guide having a flexible body which is sufficiently flexible to allow deflection of the handle for withdrawal of the boss out of mating relationship with the elongated slot. The mechanism further includes blade extracting means fixed opposite the handle guide forming a second side of the passageway and having a blade retaining projection arranged adjacent the passageway which can be actuated to prevent withdrawal of a blade from the passageway. Finally, an actuation means is included which is fixed for actuation of the blade extracting means upon deflection of the handle sufficient to disengage the boss from mating relationship with the elongated slot so that a blade mounted on the handle can be removed therefrom when the handle is withdrawn from the passageway. The present invention also includes a device including such mechanism in combination with a blade retaining and-/or disposal well which can serve as a blade dispenser and/or disposal device.

14 Claims, 7 Drawing Sheets

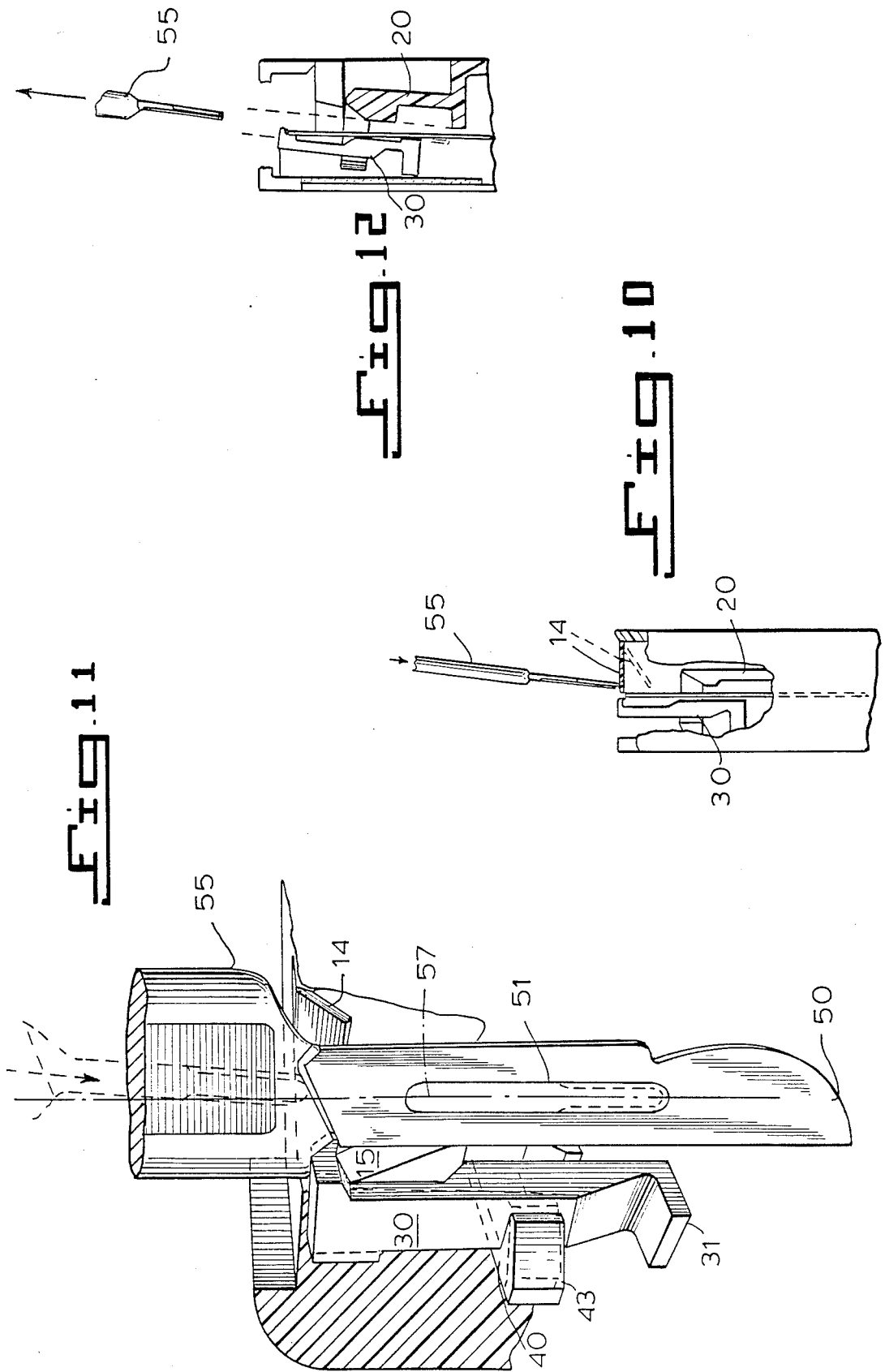

BLADE REMOVAL AND/OR MOUNTING MECHANISM AND DISPENSER, EXTRACTOR-DISPOSAL APPARATUS INCLUDING SAME

BACKGROUND OF THE INVENTION

The present invention relates to the art of cutting blade dispensing and disposal, and, in particular, to a mechanism for blade removal and/or mounting used to provide convenient storage, dispensing, and disposal apparatus for cutting blades which can be mounted on blade handles by means of a mating elongated slot and boss.

It is known in the art of cutting to provide disposable blades, such as surgical scalpel blades, commercially in several sizes, in sterile or non-sterile packaging, which are adapted to fit conventional metal scalpel handles of various sizes to form knives used for a variety of purposes in hospitals, in research laboratories, and in science departments in schools and universities. Relative to the use in hospitals, such blades are used in surgery, pathology laboratories, etc. Typically, commercially available surgical blades have a sharpened tip and cutting edge portion and a shank portion extending rearwardly therefrom. The shank portion of the blade is provided with an elongated aperture which is shaped and adapted to receive a mating elongated boss formed on the forward or attaching tip of a scalpel handle.

Generally, the elongated handle-engaging aperture of the blade can have a widened rear portion and a narrowed forward portion, the widened rear portion initially receiving the engaging boss of the scalpel handle guiding the boss forward into the narrowed forward portion of the aperture. The boss is undercut such that the edges of the narrowed forward portion of the aperture are engaged between a scalpel handle and the undercut surface of the boss. When the boss is completely inserted within the blade aperture, the rear edge of the blade aperture can be snapped over the rear of the engaging boss, thus achieving locking engagement between the blade and the scalpel handle.

In order to remove a blade of this nature from a scalpel handle, the rear edge of the blade must be separated from the handle to disengage the rear end of the blade aperture from the rear end of the boss so that the blade can then be pushed forward until the undercut boss clears the narrowed forward portion of the blade aperture permitting the blade to be cleared of the handle.

A sharp edge is essential in conducting a surgical operation. However, blades tend to lose their edge very quickly in such procedures so it is common to use several blades during a single surgical procedure. Thus, removal of a used blade from the handle and replacement of the blade with a new sterile blade is a frequent occurrence in the course of a surgical procedure.

The construction and operation of mounting and dismounting scalpel blades on blade handles present problems in that the handling of such sharp blades for mounting and removal purposes can easily cause injury to the handler. Accordingly, in the past it has been known to provide devices for removing the blade without the necessity of touching them with the hand.

For example, U.S. Pat. No. 3,172,316 to Grieshaber shows a blade removing tool formed from tubing and having an elongated handle. One end is flattened somewhat so as to provide flat opposed surfaces in which are formed opposed channel-like grooves which function as guide tracks for the boss portion of the scalpel when the tool and the scalpel boss portion are assembled. Extending longitudinally from one flat surface of the flattened end portion of the handle are two spaced-apart prongs which are inclined upwardly a slight amount. The space between the prongs is such as to permit the slender boss portion of the scalpel handle to pass therebetween, the free end of each prong being offset upwardly. The blade end of the scalpel handle can be initially inserted longitudinally through the open flat end of the tube between the channel-like grooves. The offset ends of the tool prong slidably engaging the under surface of the blade until they engage behind the innermost edge of the blade adjacent the scalpel handle. The inclination of the prongs cause the innermost edge portion of the accommodated blade to be flexed upwardly so that each edge portion thereof will clear the slender boss portion of the scalpel when the scalpel is withdrawn longitudinally from the flattened end of the tool. The blade of the scalpel is held in place by the offset ends of the prongs during withdrawal of the scalpel handle.

U.S. Pat. No. 4,180,162 to Magney shows a combination dispenser-disposal cartridge for a surgical blade which includes an elongated open-top box with means for receiving and positioning the blade in a curved position to accept the mating boss of a scalpel handle. The box also includes means for stripping a used blade from the scalpel handle and retaining it within the box for disposal. The blade is packed in the box so that it curvingly extends from the forward tip towards the shank tip to facilitate insertion of a boss of a scalpel handle into the elongated slot, which is then moved forward and withdrawn with the blade mounted on the handle. Removal of the blade from the scalpel handle is effected by inserting the scalpel handle into the aperture end of the box until the tip of the blade is engaged between the side wall and a projection extending downwardly from the top of the box at which point the handle is moved to the right so that the rear edge of the blade is stripped away from the narrowed forward portion of the scalpel handle by engagement against an upstanding blade disengaging projection formed integrally with the floor of the box. The Magney combination dispenser-disposal cartridge can prove to be somewhat ineffective in use, resulting in surgeons or assistants resorting to manual removal of the blade from scalpel handles.

Other devices include the scalpel blade remover shown in U.S. Pat. No. 4,378,624 to Klingenberg which includes a fixed block in combination with a second movable block having a slot between such blocks and a tab provided on the movable block to engage an end of the blade and move it relative to the body of the blade to disengage it from the handle. The blocks are mounted on a supporting surface beneath which a sterile disposal box may be disposed.

U.S. Pat. No. 4,318,473 to Sandel shows a surgical blade removal and disposal device which operates by inserting a handle with a blade mounted thereon through a guide means so that the rear of the blade is disposed over spaced apart shoulders after which the handle is urged downward tending to bow the blade, thus disengaging the rear of the inserted portion from the rear edge of the blade slot to allow the handle to slide relative to the blade. The blade tends to move with the handle as a result of friction between the blade and the handle until it encounters the front wall of a stop which prevents further movement of the blade rearwardly. One of the problems encountered with the Sandel blade removal device is the severe bend imposed on the blade when it is fit over the spaced apart shoulders to guide the blade to the rear stop. This causes a high degree of friction between the blade slot and the handle boss making removal of the blade very difficult.

U.S. Pat. No. 4,344,532 to Eldridge, Jr., et al. discloses a surgical blade remover having a wedge shaped support member which tapers from its front side to its back side. The support has one or more mutually parallel latitudinal slots open at one end and along their length extending from the front side of the support to its interior. The slots are sized to receive the tang of the blade holder while preventing the blade itself from passing therethrough and the surface of each of the support members bordering the slot is covered with an adhesive which holds the blade in place while the handle is pivoted downward in the slot away from the blade. In certain embodiments, the slots are shown to have modifications contoured to compliment the shape of the blade and/or to provide a notch to receive a portion of the hilt of the blade in order to assist in blade removal.

U.S. Pat. No. 4,120,397 to Neumann shows a unit for accommodating disposable blade-like articles in which the underside of a blade such as a scalpel blade, slidably engages a resilient tongue-like element which is deflected upwardly. The tongue-like element has mounted thereon cam means having surfaces which can be pushed against the blade to unseat the rear of the blade away from a boss on the blade handle. Once the tongue-like member is fully depressed thereby deflecting the rear of the blade downwardly, the scalpel handle can be removed, abutting the rear of the blade against the inside surface of a panel, thus unseating the blade from the boss and disassembling the blade from the handle.

U.S. Pat. No. 4,106,620 to Brimmer, et al. shows a surgical blade dispenser and disposal assembly which includes blades individually positioned and supported within the box between a slot in a forward wall and a slot in a rearward wall which holds the blades in such a fashion as to slightly deform them in a lateral curve for receipt of a boss of a surgical blade holder in the elongated slot formed in the body of the blade. The blades can be removed by insertion of the blade bearing handle through the aperture and wedged rearwardly against projecting ears. The handle is then moved laterally to separate the rear of the blade from the boss and remove the handle completely off the blade. This device has proved to be cumbersome and the removal apparatus does not provide for efficient removal of the blades.

It is therefore an object of the present invention to provide a scalpel blade dispenser by which scalpel blades can be quickly and easily mounted onto a scalpel blade handle.

It is another object of the invention to provide a scalpel blade extractor which facilitates easy removal of the blade from a blade handle.

Another object of the invention is to provide a scalpel blade dispenser holder which gives quick and easy access to a variety of scalpel blades.

Commensurate with the previous object of the invention, it is a further object to provide a device by which stored blades can be easily identified.

A further object of the present invention is to provide for safe storage of scalpel blades during the course of surgical operations.

Another object of the invention is to facilitate the safe disposal of used and contaminated scalpel blades.

Another object of the invention is to permit the quick and accurate inventory of scalpel blades usually conducted at the conclusion of surgical operations.

Other and further objects of the present invention will become apparent to those skilled in the art in view of the disclosure of the invention as set forth herein.

SUMMARY OF THE INVENTION

The present invention includes a mechanism which can be used for both mounting and removing a blade having an elongated slot mounting means from a blade handle which has a mounting boss for insertion into the elongated slot. The mechanism includes a handle guide which forms one side of a passageway for insertion of the blade handle, the handle guide having a flexible body portion which is sufficiently flexible to allow deflection of the handle for withdrawal of the boss out of mating relationship with the elongated slot of the blade. Another element of the mechanism is a blade extracting means fixed opposite the handle guide which forms a second side of the passageway, the extracting means having a blade retaining projection arranged adjacent the passageway which can be actuated to prevent withdrawal of a blade from the passageway. The mechanism further includes a actuation means fixed for actuation of the blade extracting means upon deflection of the handle sufficiently to disengage the boss out of a mating relationship with the elongated slot. As a consequence a blade mounted on a handle can be removed therefrom when the handle is withdrawn from the passageway while the extracting means is being actuated.

A device of the present invention can also include a well for holding a blade in a position for mounting on a handle as well as for receiving a blade once used. Alternatively, the well can be used as a disposal receptacle when the mechanism is used merely as a blade disarmer. When it is contemplated to provide a dispensing/disposal apparatus, the well can also include a blade support which holds a blade in a mounting position while preserving the blade's cutting edge.

Referring to the individual elements of the mechanism, the blade extracting means includes a flexible arm extending from a point at one end of the passageway and extends along the passageway to an operative end, the blade retaining projection being fixed at the operative end so that it is positioned out of the passageway in the unactuated condition and so that it can be drawn over the passageway when actuated. The actuation means, in turn, includes a latch means secured to, for example, the handle guide, the latch means including a yoke extending around the passageway and a yoke tab extending around the blade removal hook arm whereby the tab is drawn into actuating contact with the arm when the handle guide is deflected away from the blade extracting means. Alternatively, the latch means can be secured to the blade removal arm while the yoke extends around the passageway and the yoke tab extends around the handle guide. The yoke tab can extend around either the arm or the handle guide a distance sufficient to permit insertion of the handle through the passageway without actuating the actuating arm.

The mechanism can be included in a housing to provide a combination blade dispenser and disposal device. The housing can be a sterilizable clear container wherein the blades can be visibly packaged and sterilized. A reclosable lid can be formed over the entire set of blade openings with a weakened portion attaching it to the housing on one side and an opening on the opposite side for articulable movement over the blades. Preferably, the device can include at least four blades for use in an operating environment.

It has been found that the device can preferably be from about 2" to about 2¾" high, from about 3" to about 4" long, and from about 1¾" to about 2¾" wide at the base, and can be provided with an adhesive on the bottom surface for securing the device in place during use.

As a result of the present invention a medical operating team can be provided with quick and easy access to a variety of scalpel blades in the device which permit the safe handling of the blades by mechanically mounting and dismounting as required. The blades can be identified as new or used and the device permits a blade count at the conclusion of the operation to be performed more quickly and accurately while allowing for the safe storage and disposal of the used scalpel blades.

In another embodiment, the invention can be used to provide a blade disposal container which contains the mechanism described above for disarming a blade from a handle.

For a better understanding of the present invention, together with other and further objects, reference is made to the following description, taken in conjunction with the accompanying drawings, and its scope will be pointed out in the appended claims.

BRIEF DESCRIPTION OF THE DRAWINGS

Preferred embodiments of the invention have been chosen for purposes of illustration and description and are shown in the accompanying drawings wherein:

FIGS. 10 and 11 show the steps involved in mounting a blade onto a blade handle;

FIG. 12 shows the operation of the mechanism for removal of the blade from the handle;

DETAILED DESCRIPTION OF THE INVENTION

Figure 1:
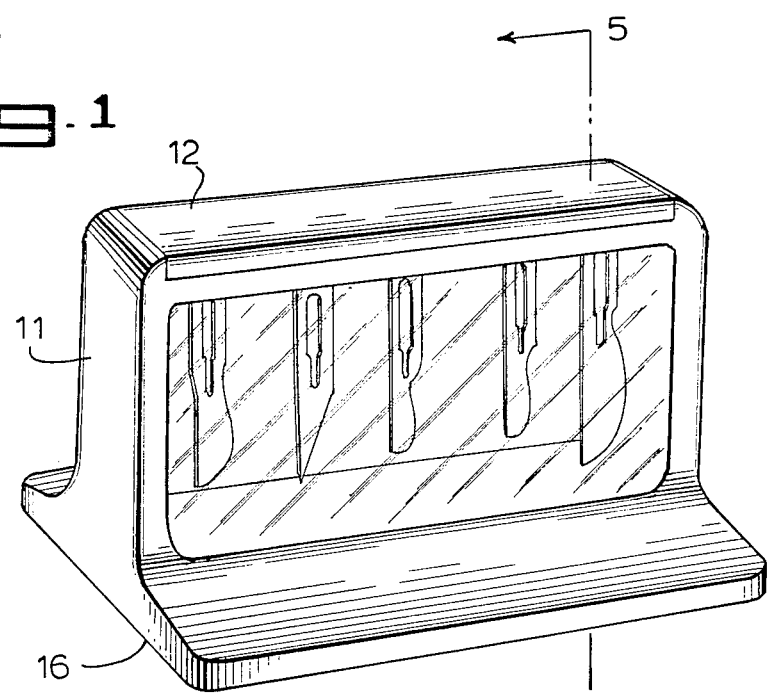
FIG. 1 is a perspective view of a blade dispensing-/disposal apparatus in accordance with the present invention.

To the extent possible, the same numerals will be used throughout the figures when referring to the same parts. Referring to FIG. 1 there can be seen a device constructed in accordance with the present invention for packaging a series of blades, such as scalpel blades, for mounting on a scalpel blade handle, and for dismounting the blade from the handle and disposal after use. In FIG. 1 the device is shown with five blades which can be packaged, sterilized, and delivered to the operating environment for selection and use by the operating team. The dispenser can have a transparent housing 11 whereby the different size and type of blades can be conveniently viewed by the surgeon or assistant.

Figure 2:
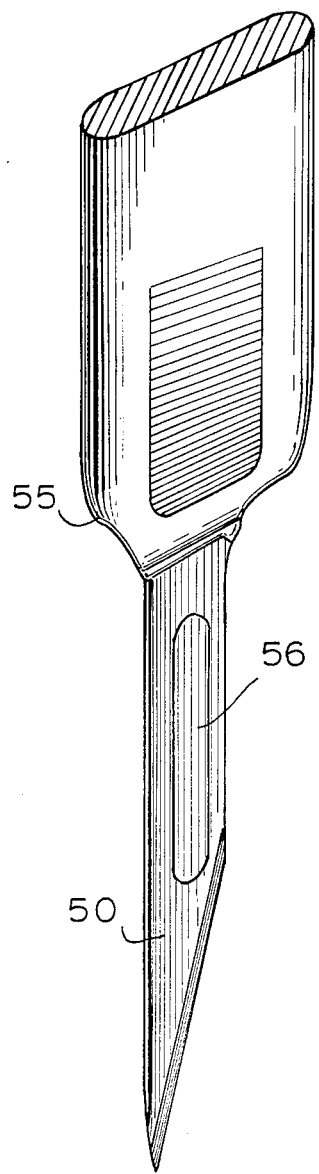
FIG. 2 is a perspective view of a handle with a blade mounted thereon.
Figure 3:
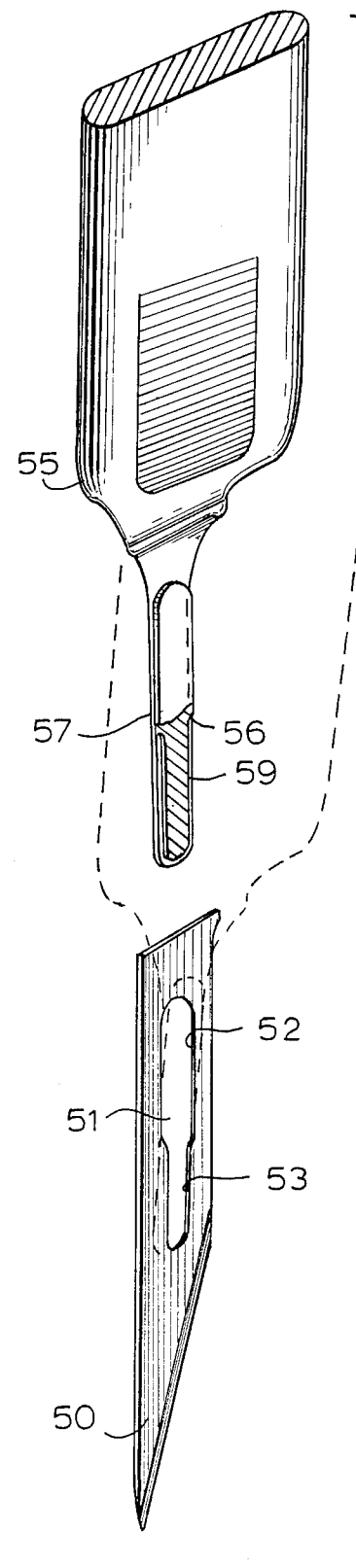
FIG. 3 shows the relationship of the blade and the handle in the disassembled condition.

FIGS. 2 and 3 show the relationship of the scalpel blade to the scalpel blade handle in a fully assembled position in FIG. 2, and in a disassembled configuration in FIG. 3. Referring to these figures there can be seen a blade 50 having an elongated aperture 51 with a reduced sized section 53 and an enlarged section 52. It is also known that the elongated aperture can have three variations in aperture size rather than merely two as shown in FIG. 3.

A blade handle 55 is shown with an elongated forward portion 57 provided with a peripheral mounting slot 59. The peripheral slot 59 can be formed by provision of a raised boss 56 having the undercut peripheral slot 59. The boss 56 extends outwardly from the forward end portion 57. Referring specifically to FIG. 3 there is shown a partial cutaway of the boss 56 to show the peripheral mounting slot 59 formed as an undercut of the boss 56. In order to mount the blade 50 onto the handle 55, the raised boss portion 56 must be directed into the enlarged portion 52 of the elongated aperture 51 and thrust forward so that the entire body of raised boss 56 is inserted into the elongated aperture 51. The narrowed portion 53 of the elongated aperture is frictionally engaged by the peripheral slot 59 to secure the blade 50 on the handle 55. It is noted that the blade is secured on the handle when the rear portion 52 of aperture 51 drops over the rear portion of the raised boss 56 and snaps into mating relationship therewith.

Figure 4:
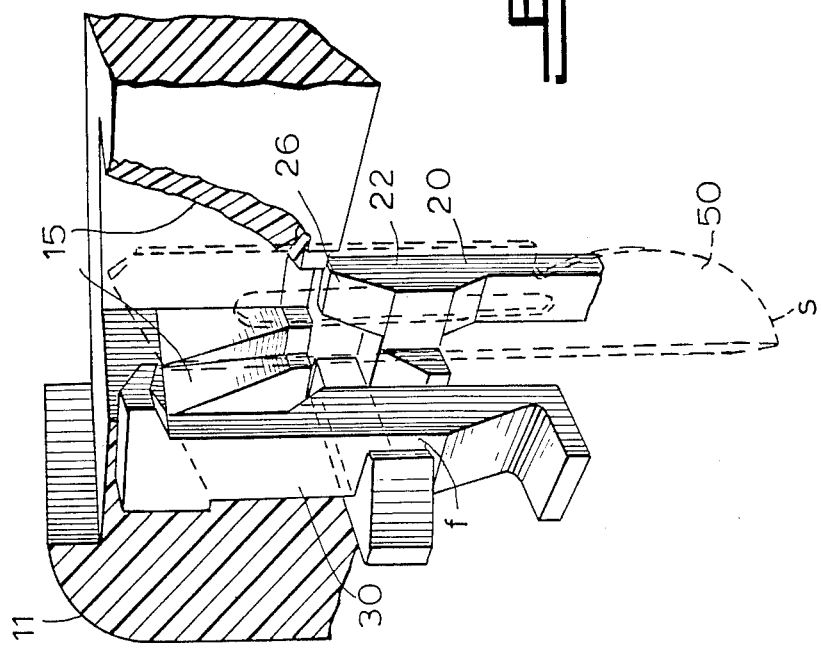
FIG. 4 is a perspective view of the operative mechanism of the present invention with the scalpel blade shown in phantom in order to depict the relationship of the blade to the mechanism.
Figure 7:
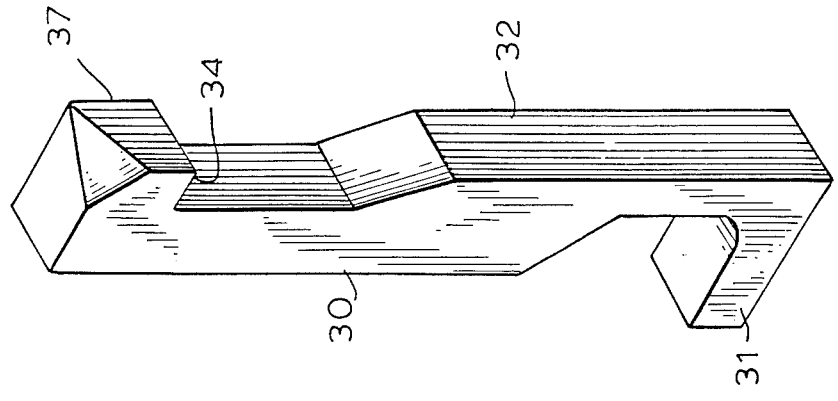
FIG. 7 is an exploded isometric view of a blade hook assembly portion of the mechanism.
Figure 6:
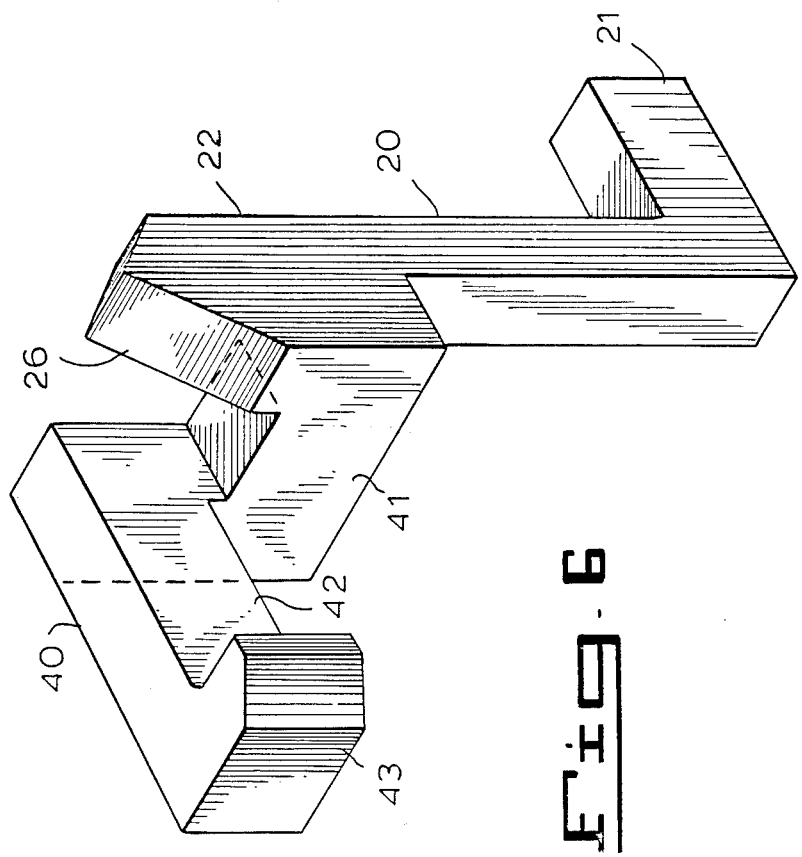
FIG. 6 is an exploded isometric view of a handle guide and latch hook assembly of the operative mechanism.

Referring to FIG. 4, the operative mechanism of the present invention is shown with a blade 50 shown in phantom therein. Reference is also made to FIG. 6 and 7 to show the different elements of the operative portion shown in exploded isometric view. In particular, the operative mechanism includes a handle guide assembly 20 having a lower frame 21, which can be part of a molded base portion, and an upper handle guide 22 having a guiding surface 26. The handle guide assembly is fixed within housing 11 opposite a blade hook assembly 30 to form one side of a passageway for the blade and blade handle.

The blade hook assembly 30, in turn, includes a housing support part 31, as well as a leg portion 32 which extends upwardly to a blade removal hook 37 having a blade removal surface 34.

A third portion of the operative mechanism of th present invention is a latch hook assembly 40 which is rigidly fixed to the handle guide 22 by means of a latch bar 41 and continues perimetrically around the blade passage by means of a latch extension 42. At the end of the latch extension 42 is a latch hook 43, which extends around the leg 32 a distance "f" from the leg 32 to permit deflection of the handle guide assembly 20 a distance sufficient to permit insertion of a handle tip in the passageway for mounting a blade thereon.

Figure 8:
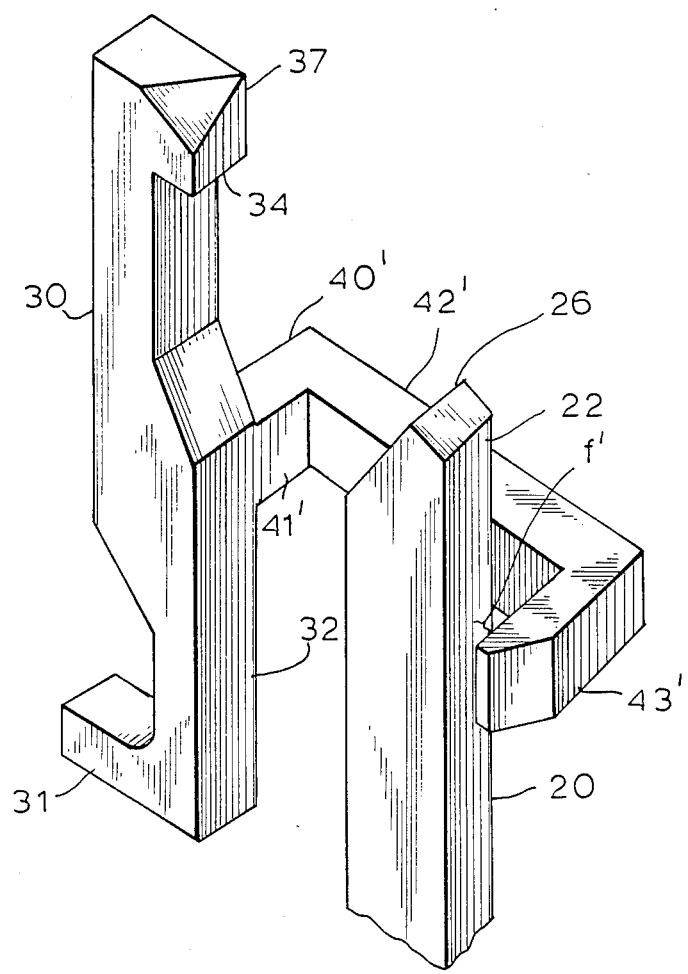
FIG. 8 shows an alternative embodiment of the operative mechanism of the present invention.

In FIG. 8, an alternative embodiment of the present invention is shown with the latch hook assembly rigidly affixed to the blade removal hook rather than the handle guide assembly. These parts of the configuration shown in FIG. 8 which have been rearranged are designated with primed numbers to indicate that they are parts with similar function, but with a different configuration.

Figure 5:
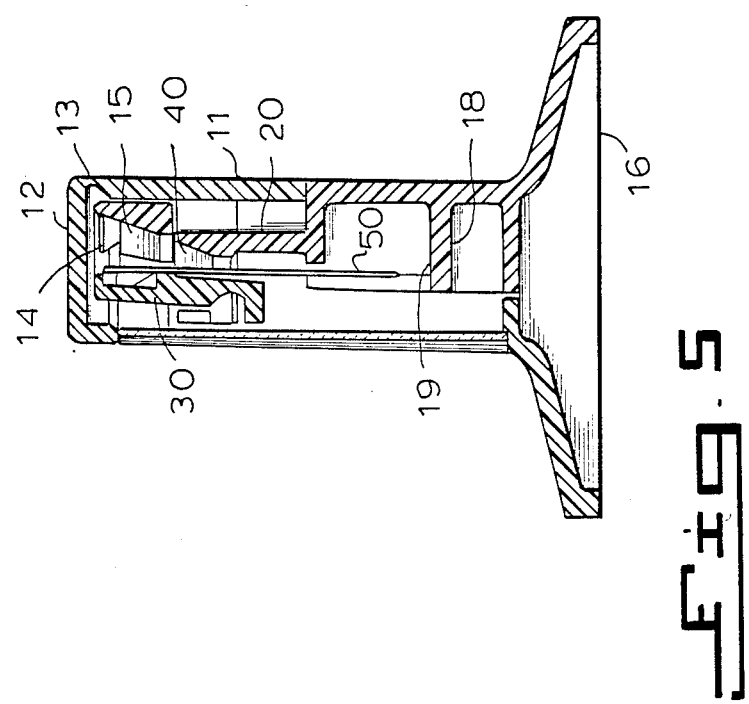
FIG. 5 is a side elevational cross-section of the apparatus shown in FIG. 1 taken along lines 5—5.

Referring to FIG. 5 there can be seen a side elevational view in cross-section of the apparatus as shown in FIG. 1 taken along lines 5—5 which shows the relationship of the operative portions of the mechanism to the housing 11. In this view the blade is shown resting on a blade platform 18, which can include a blade support projection 19. The support projection 19 is located on the platform 18 at a position wherein the blade rests thereon at location "s" (seen in FIG. 4) which is essentially unused during a procedure, e.g., usually between the point and the cutting "belly" of the blade.

Figure 9:
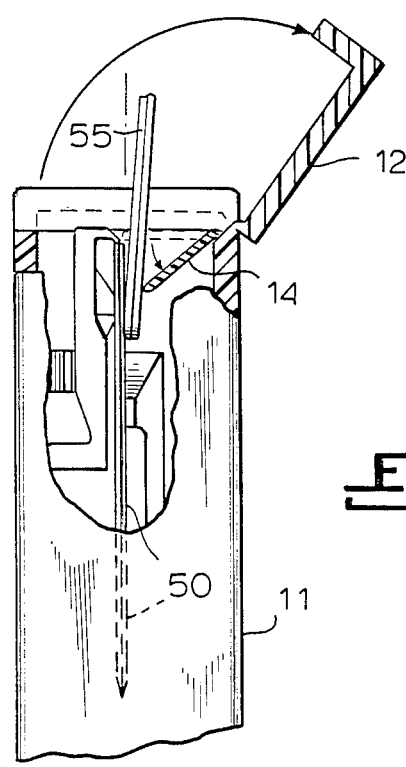
FIG. 9 is an end view of the apparatus shown in FIG. 1 with partial cutaway to depict the operation of the lid and the blade usage indicator tab.

Further features of the present invention include in the preferred mode, a lid 12 preferably, having a living hinge 13, which can be raised rearwardly (see FIG. 9) to expose a blade use indicator tab 14 located immediately above the packaged blade. In operation, when the handle is inserted to mount the blade thereon, the blade indicator tab 14 is depressed downwardly to be captured between converging shoulders 15 provided in the housing, so that once depressed, use of the blade is memorialized by the dowwnwardly-retained tab.

The operation by which a blade is mounted on the handle is shown in FIGS. 10 and 11. In particular, in FIG. 10, the front portion 57 of a blade handle 55 is thrust downwardly to depress the blade indicator tab 14 and to gain access into the passageway between the handle guide assembly 20 and the hook removal assembly 30. Referring now to FIG. 11, the handle can be seen as it has been engaged with the elongated aperture 51 of the blade 50. The tab 14 which has been depressed is retained in the depressed condition by frictional fit between converging shoulders 15. Since there is a distance "f" between the leg 32 and the latch hook 43, the handle guide can be deflected to a certain extent without activating the blade removal assembly 30. Once the blade has been secured on the front end 57 of the handle 55, the entire assembly can be vertically removed from the mechanism.

The removal of a blade from a handle is explained with reference to FIG. 12. The blade and handle assembly can be inserted once again through the opening provided by the permanently depressed tab 14 and into the passageway between the handle guide assembly 20 and the blade hook assembly 30. Once the blade is fully inserted into the passageway, the handle 55 can be deflected toward the handle guide assembly 20 and away from the blade removal assembly 30, i.e., to the right as shown in FIG. 12. As a result of this deflection, the handle 55 strikes against the upper handle guide 22 thereby urging the handle guide assembly with the latch hook assembly 40 rigidly fixed thereto away from the passageway. The latch hook 43, thereby traverses through the distance "f" and strikes the rear of leg 32 of blade removal hook assembly 30 thereby urging it over the passageway as shown in FIG. 12. When the blade handle is deflected out of the passageway, the, rear portion of the raised boss 56 is simultaneously disengaged from the rear portion of the elongated aperture 51, thus permitting a disengaging movement of the handle from the blade. In the present mechanism the disengaging movement is a vertically upward pull of the handle out of the passageway, which, in the condition shown in FIG. 12 causes the top end of the blade 50 to strike against the blade removal surface 34 thereby preventing the blade from being lifted from the passageway. It should be noted that since only a slight deflection of the handle away from the blade is required to disengage the boss 56 from the aperture 51, and to simultaneously actuate the blade removal assembly, there is but a minimal increase in the friction between the narrow portion 53 of the blade aperture 51 and the undercut peripheral slot 59 of the boss 56. Thus, as a result of the actuation of the removal assembly 30 and the low-frictional-fit condition of the blade 50 on the mounting boss 56, the handle can be very easily withdrawn and disassembled from the blade without touching the blade itself.

Figure 14:
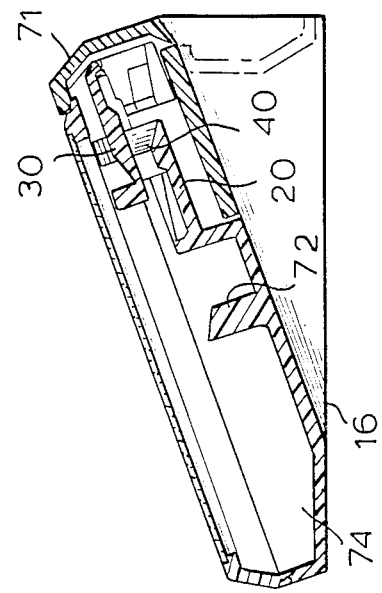
FIG. 14 is a cross-section of the embodiment shown in FIG. 13 taken along lines 14—14.
Figure 13:
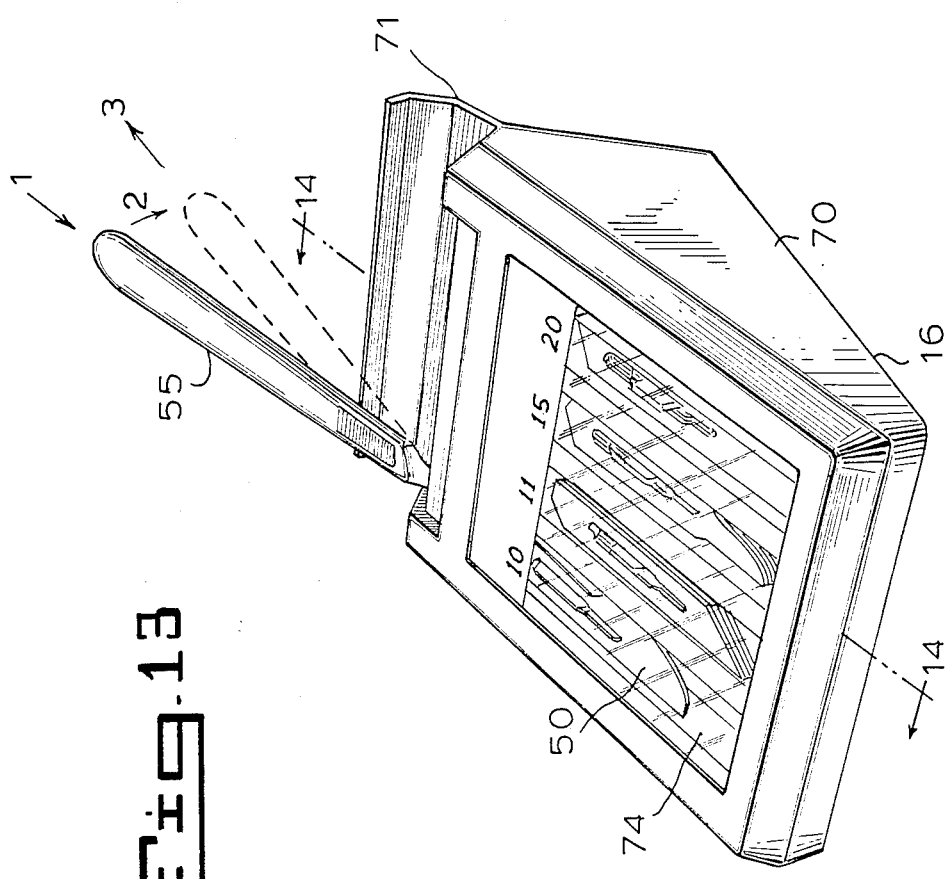
FIG. 13 is yet another embodiment of the present invention which is useful as a blade disarming and disposal apparatus.

Referring to FIG. 13 there is shown a further embodiment of the present invention which can be used merely as a disposal apparatus for removal and storage of used blades. In particular there is shown device 70 with a lid 71 which can be rotated rearwardly from the top of the apparatus 70 as shown in phantom in FIG. 14. Once the lid is opened, a fully assembled blade and handle can be inserted into the mechanism and manipulated as shown in FIG. 13 to remove a blade. Additionally, in the configuration shown in FIGS. 13 and 14 a blade retaining post 72 can be provided in receiving wells 74 in order to maintain the blades therein in a coherent stack.

In either of the preferred embodiments, when the housing is made of a transparent material, the blades disposed of can be easily inventoried after a procedure to facilitate accountability. Further with regard to the preferred embodiments, the composite housing unit can have an adhesive bottom 16 which holds it firmly in place for both the blade mounting and dismounting procedure as described above. The dispensing device with new blades packaged therein can be optionally covered with a sterile wrap material and subjected to sterilization procedure by use of ethylene oxide, radiation, etc.

Thus, while there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

We claim:

1. A mechanism for removing a blade having an elongated slot mounting means from a blade handle which has a mounting boss for insertion into said elongated slot, comprising
a blade well for receipt of said blade upon dismounting from said handle,
a handle guid forming one side of a blade and handle passageway into said well said handle guide having a flexible body portion being sufficiently flexible to allow deflection of said handle away from said blade for withdrawal of said boss out of mating relationship with said elongated slot,
blade extracting means located on a side of said passageway generally opposite said handle guide, said extracting means having a blade retaining projection arranged adjacent said passageway adapted to be actuated to a position to prevent withdrawal of said blade from said well, and actuation means located fore actuation of said blade extracting means as a direct result of the deflection of said handle sufficient to disengage said boss out of mating relationship with said elongated slot, whereby a blade mounted on said handle is engaged by said retaining projection for removal as said handle is withdrawn from said passageway.

2. The mechanism of claim 1 wherein said blade extraacting means further comprises a flexible arm extending from a point adjacent said well along said passageway to an operative end, said blade retaining projection fixed at said operative end so that the projection is adapted to be positioned out of said passageway in the unactuated condition and so that the projection is adapted to be drawn over said passageway when actuated whereby said blade is prevented from being removed from said passageway.

3. The mechanism of claim 2 wherein said actuation means comprises latch means secured to one of said handle guide and said blade extracting means, said latch means including a yoke extending around said passageway and a yoke tab extending around one of said flexible arm and said handle guide whereby said tab is drawn into actuating contact with one of said flexible arm and said handle guide when said handle guide is deflected away from said blade extracting means.

4. The mechanism of claim 3 wherein said yoke tab extends around one of said flexible arm and said handle guide a distance sufficient to permit insertion of said handle throu said passageway without actuating said flexible arm.

5. The mechanism of claim 4 wherein said housing is transparent and wherein there are more than one said mechanism.

6. The mechanism of claim 1 which is mounted in a housing to provide a combination blade dispenser and disposal device.

7. A mechnaism for mounting and removing a blade having an elongated slot mounting means from a blade handle which has a mounting boss for insertion into said elongated slot, comprising a blade well for holding said blade in a position for mounting on said blade handle and for receipt of said blade upon dismounting from said handle, a handle guide forming one side of a blade and handle passageway into said well, said handle a guide having a flexible body portion being sufficiently flexible to allow insertion of said handle boss into mating relationship with said elogented slot and to allow deflection of said handle away from said blade for withdrawal of said boss out of mating relationship wtih said elongated slot, blade extracting means located on a side of said passageway generally opposite said handle guide, said extracting means having a blade retaining projection arranged adjacent said passageway adapted to be actuated to a position to prevent withdrawal of a blade from said well, and actuation means located for actuation of said blade extracting means as a direct result of the deflection of said handle sufficient to disengage said boss out of mating relationship with said elongated slot, whereby a blade mounted on said handle is engaged by said retaining projection for removal as said handle is withdrawn from said passageway.

8. The mechanism of claim 7 wherein said blade extracting means further comprises a flexible arm extending from a point adjacent said well along said passageway to an operative end, said blade retaining projection located at said operative end so that the projection is adapted to be positioned out of said passageway in the unactuated condition and so that the projection is adapted to be drawn over said passageway when actuated whereby said blade is prevented from being removed from said passageway.

9. The mechanism of claim 8 wherein said actuation means comprises latch means secured to one of said handle guide and said blade extracting means, said latch means including a yoke extending around said passageway and a yoke tab extending around one of said flexible arm and said handle guide whereby said tab is drawn into actuating contact with one of said flexible arm and said handle guide when said handle guide is deflected away from said blade extracting means.

10. The mechanism of claim 9 wherein said yoke tab extends around one of said flexible arm and said handle guide a distance sufficient to permit insertion of said handle through said passageway without actuating said flexible arm.

11. The mechanism of claim 7 wherein said well comprises a blade support which bears a blade in an upright position for mounting at a point along said blade which preserves a useable portion of said blade's cutting edge.

12. The mechanism of claim 11 wherein said housing is transparent and wherein there are more than one said mechanism.

13. The mechanism of claim 12, wherein the device is wrapped and sterilized.

14. The mechanism of claim 7 which is mounted in a housing to provide a combination blade dispenser and disposal device.

* * * * *